United States Patent
Chen et al.

(10) Patent No.: US 11,420,938 B2
(45) Date of Patent: Aug. 23, 2022

(54) METHOD AND PRODUCTION SYSTEM FOR FULLY RECOVERING AND TREATING TAURINE MOTHER LIQUOR

(71) Applicant: QIANJIANG YONGAN PHARMACEUTICAL CO LTD, Qianjiang (CN)

(72) Inventors: Yong Chen, Qianjiang (CN); Xiquan Fang, Qianjiang (CN); Shaobo Li, Qianjiang (CN); Feng Liu, Qianjiang (CN); Xiaojun Jiang, Qianjiang (CN); Wei Zhou, Qianjiang (CN)

(73) Assignee: QIANJIANG YONGAN PHARMACEUTICAL CO LTD, Hubei Province (CN)

( * ) Notice: Subject to any disclaimer, the term of this patent is extended or adjusted under 35 U.S.C. 154(b) by 0 days.

(21) Appl. No.: 16/914,224

(22) Filed: Jun. 26, 2020

(65) Prior Publication Data
US 2021/0114978 A1    Apr. 22, 2021

(30) Foreign Application Priority Data
Oct. 16, 2019    (CN) .......................... 201910986942.4

(51) Int. Cl.
  *C07C 303/44* (2006.01)
  *C07C 303/06* (2006.01)
  *C07C 305/00* (2006.01)

(52) U.S. Cl.
  CPC .......... *C07C 303/44* (2013.01); *C07C 303/06* (2013.01); *C07C 305/00* (2013.01)

(58) Field of Classification Search
  CPC .... C07C 303/44; C07C 303/06; C07C 305/00
  USPC .......................................................... 562/124
  See application file for complete search history.

(56) References Cited

U.S. PATENT DOCUMENTS

2015/0299114 A1* 10/2015 Hu ........................ C07C 303/32
                                                          562/104

OTHER PUBLICATIONS

European Search Report from corresponding European Application No. 20153990.5, dated Jul. 21, 2020.
Official Office Action from corresponding European Application No. 20153990.5, dated Feb. 10, 2021.

* cited by examiner

*Primary Examiner* — Deborah D Carr
(74) *Attorney, Agent, or Firm* — Porter Wright Morris & Arthur LLP

(57) ABSTRACT

A method and a production system for recovering and treating taurine mother liquor, which is used for the process of ethylene oxide taurine production process. As for the treatment of the last mother liquor of taurine, add alkali firstly to the last mother liquor of taurine and then acid to form salt, or add salt directly; then concentrate and crystallize and filter, to remove lots of impurities in taurine mother liquor. This solves the problem of separating impurities, greatly shortening the time of removing impurities. The last mother liquor can also be decolorizes and additional impurities removes by activated carbon, and the removal of salt by mixing ammonia into the mother liquor to obtain the pure taurine mother liquor, thereby recovering the mother liquor and increasing the product yield.

20 Claims, 6 Drawing Sheets

METHOD AND PRODUCTION SYSTEM FOR FULLY RECOVERING AND TREATING TAURINE MOTHER LIQUOR

BACKGROUND

The present disclosure relates to a production method in a chemical process for the synthesis of taurine, in particular to the mother liquor produced by the production of taurine by an ethylene oxide method, a method and a production system for removing impurities and recycling thereof.

BACKGROUND OF THE INVENTION

Taurine (2-aminoethanesulfonic acid) is the most abundant sulfur-containing free amino acid in body cells. The chemical synthesis route of taurine mainly includes an ethylene oxide method and an ethanolamine method. Among them, the preparation of taurine by the ethylene oxide process comprises three steps:

(1) Utilizing ethylene oxide as a starting material, an addition reaction of ethylene oxide and sodium hydrogen sulfite generates sodium isethionate:

Main Reaction:

$$CH_2CH_2O+NaHSO_3 \rightarrow HOCH_2CH_2SO_3Na$$

Addition Side Reaction:

$$CH_2CH_2O+H_2O \rightarrow HOCH_2CH_2OH$$

(2) Aminolysis of sodium isethionate to generate sodium taurate:

$$HOCH_2CH_2SO_3Na+NH_3 \rightarrow H_2NCH_2CH_2SO_3Na+H_2O$$

Ammonolysis Side Reactions:

$$2HOCH_2CH_2SO_3Na+NH_3 \rightarrow HN(CH_2CH_2SO_3Na)_2+2H_2O$$

$$3HOCH_2CH_2SO_3Na+NH_3 \rightarrow N(CH_2CH_2SO_3Na)_3+3H_2O$$

(3) Taurine is generated through acidification, for example using hydrochloric acid or, more typically, sulfuric acid, to neutralize the sodium taurate and generate taurine and the inorganic salt. For example, when sulfuric acid is used a taurine solution is produced:

$$2H_2NCH_2CH_2SO_3Na+H_2SO_4 \rightarrow 2H_2NCH_2CH_2SO_3H+Na_2SO_4$$

By-products are inevitably produced in the addition and synthesis reactions, including ethylene glycol, ethylene glycol polymers and so on. The aminolysis reaction is a reversible reaction. About more than 20% of sodium isethionate will enter step 3 of the production process. After the aminolysis reaction the ammonia solution is neutralized by sulfuric acid (or another acid) to produce a taurine solution (step 3 above). After the crude taurine is separated and extracted from the mother liquor, the mother liquor is concentrated and crystallized for 1-3 times, with crude taurine separated and extracted from the mother liquor after each crystallizing step, thereby generating the last mother liquor. Thus, the "the last mother liquor" is the solution remaining after the mother liquor has been concentrated and solid taurine crystallized and removed at least once. In some instances the concentration/crystallization process is repeated at least one time more or at least two times more to generate the last mother liquor. The last mother liquor will mainly include taurine, along with the impurities sodium isethionate, sodium sulfate, sodium iminodisulfonate, ethylene glycol and polyethylene glycol, and trace metal ions, which are highly polluting emissions. When the existing production method adopts the mother liquor circulation, the cumulative increase of by-products will occur. When the by-products reach a threshold level, discharging part of the mother liquor is necessary, resulting in waste and pollution.

Chinese patents CN101508657, CN10158658, CN10158659 and CN101486669 describe a process of generating taurine and sodium sulfate by neutralizing sodium taurate with sulfuric acid. The crude taurine can be easily generated by filtering the crystal suspension liquor after cooling. However, the discarded mother liquor still contains taurine, sulfate and other organic impurities.

On the use of mother liquor, *Research on Taurine Ammonolysis Process,* published in Issue 5, Volume 44 of *Shandong Chemical Industry,* 2015, (Author: Liu Fuming, Xie Limin), specifies in detail the process of taurine reaction, and the other organic impurities in the reaction, such as ethylene glycol and polyethylene glycol, and analyzes the effect of recycling mother liquor application on yield. The higher the content of mother liquor in the reaction system, the higher the product yields. In the actual production process, the amount of mother liquor cannot be infinitely increased. As the content of mother liquor increases, by-products in the reaction system increase greatly, and the output of the last mother liquor in the production process can only meet the maximum 9.0% (v/v) set of dosage. Considering comprehensive production costs and yield quality, it is most appropriate to choose the mother liquor content of 6.3%-8.3% (v/v). Therefore, the removal of impurities in the mother liquor is a prerequisite for increasing the application of the mother liquor, otherwise the increase in the amount of application will cause more by-products in production and the production will be more unstable.

Chinese patent CN107056659A describes a method for neutralizing sodium taurate by ion exchange to generate taurine, and then recycling the mother liquor to further increase the yield. The process route mainly avoids the generation of sulfate, recycles sodium atoms therein, and greatly saves raw materials such as sulfuric acid and sodium hydroxide, wherein the extracted mother liquor is returned to the aminolysis reaction as a raw material. However, the process does not avoid the occurrence of side reactions such as addition and synthesis reactions, and the mother liquor still needs to be subjected to impurity removal treatment.

With regard to the impurity removal treatment of the mother liquor, Chinese Patent CN105732440 discloses a method for producing taurine by fully recovering the mother liquor, which mainly removes impurities by neutralization in the second stage to obtain crude taurine, and the mother liquor is subjected to pressure filtration and catalysis to further remove sodium sulfate. After that, the sodium is reused in the synthesis section. Among them, the removal effect of ethylene glycol and other organic polymers therein by the second-stage neutralization and removing impurity is limited.

In summary, although the current taurine preparation process is relatively mature, there are still many deficiencies in the separation and purification of taurine and the recycling of the mother liquor. In particular, the viscosity of organic impurities in the last mother liquor produced by the system for producing taurine is high, and it is difficult to separate the impurities in a large-scale production. It is urgent to seek an effective solution.

SUMMARY

The present disclosure provides a pretreatment process and system for the last mother liquor of taurine, which can effectively reduce the viscosity of the last mother liquor, remove some impurities at the same time, and greatly improve the recovery treatment efficiency.

Further, the present disclosure provides an impurity-removal and mother liquor recovery method and system using the pretreatment method to achieve full recovery of the mother liquor (i.e., all of the mother liquor is returned to the aminolysis step).

After extensive research and experimentation, the inventors unexpectedly discovered a method for removing and recovering taurine from the mother liquor, adding a pretreatment process for the mother liquor (i.e., prior to its return to the aminolysis step) in the existing ethylene oxide process for preparing taurine. The viscosity of the last mother liquor is lowered, and then the subsequent decolorization and impurity removal treatment are performed. The liquor can then be efficiently recycled to the aminolysis reaction step.

A method for fully recovering and treating taurine mother liquor in an ethylene oxide process for producing taurine by treating the last mother liquor of taurine comprises the following steps:

(a) adding alkali firstly and then acid to the last mother liquor of taurine to form a salt in the solution, or adding a salt directly to the last mother liquor of taurine, wherein the generated or added salt is used to reduce the filtration resistance;

(b) concentrating and crystallizing the material collected in step (a); and (c) obtaining clear last mother liquor of taurine through filtration.

In one embodiment, the reaction temperature of step (a) is 50° C.-95° C., and the pH value after acid addition is 7.0-10.5. In another embodiment, the reaction temperature is 50° C.-75° C., and the pH value is 8.5-10.0.

The amount of the alkali added in the said step (a) can be from 5% to 50% (by volume) of the volume of the last mother liquor of taurine, or from 15% to 35%, of the volume of the last mother liquor of taurine.

Further, the alkali in step (a) can be any one of sodium hydroxide, potassium hydroxide, lithium hydroxide, sodium carbonate, potassium carbonate, lithium carbonate and so on, or the mixture of any two or more thereof. The acid can be sulfuric acid, hydrochloric acid, an organic acid, etc. Salt is formed by the reaction of the alkali with the added acid. For example, sodium hydroxide reacts with sulfuric acid to form sodium sulfate, and potassium hydroxide reacts with sulfuric acid to form potassium sulfate, etc. As an alternative to forming salt in the solution by adding an alkali and an acid, salt can be added to the last mother liquor. For example, the amount of the added salt can be 530 mol-5300 mol per $m^3$ of the last mother liquor. In most instances, liquid sodium hydroxide and sulfuric acid area added successively, according to the principle of chemical acid-alkali reaction, whereby the sodium in the last mother liquor is formed into sodium taurate, and then sodium sulfate is formed when the acid is added. Forming the salt in this manner has the advantage of not increasing the production system. New impurities are more conducive to recycling applications.

In one embodiment, in step (b) water is evaporated from, and the last mother liquor of taurine condensed such that 30-60%, or 35%-45% of the water is removed, and the solution is concentrated about 1.4-2.5, or 1.5-1.8 times, to obtain the crystallization solution.

Preferably, in step (b), the salt-containing, concentrated, crystallization solution (i.e., the mother liquor) is cooled and crystallized.

Subsequently, the mother liquor after the pretreatment is further subjected to decolorization and impurity removal treatment using activated carbon. In this step (c), the last mother liquor of the taurine generated in step (b) is decolorized by adding activated carbon under cooling conditions, and the pH value is adjusted to 9.0-10.5 by adding alkali, and then filtered.

The cooling condition in step (c) means that the temperature is lower than the temperature of the previous step. For example, the system processing temperature is controlled to be 15-25° C., or 18-22° C.;

The activated carbon decolorization and alkali-filtered outlet liquid can be subjected to an ammonia-mixing treatment, and a solid-liquid separation performed to generate the mother liquor after the impurity removal. All of the mother liquor is then returned to the aminolysis step. When ammonia-mixing treatment is required, liquid ammonia or ammonia is added to the mother liquor, and the mass to volume ratio of ammonia to liquid is 15 g/100 ml (15%), or 17-19 g/100 ml (17-19%), in order to remove impurities such as salt.

During the treatment process, the by-products of the reaction process are removed. Because the viscosity of the by-products is high, separation is normally difficult, which is unfavorable for industrial production. The method of the present disclosure combines the natures of solubilities of taurine, sulfate, impurities and the like at different temperatures, concentrations and pH conditions, and controlling the temperature, concentration and pH value of the reaction in each step, so that the impurities can be precipitated, and the active ingredient (taurine) is not precipitated, thus creating conditions for the separation of impurities and active ingredients. Thus, during the treatment process, impurities in the last mother liquor solution react with the liquid alkali to make the impurities in the solution exist as a sodium salt, and then the solution is neutralized using sulfuric acid, which will form sodium sulfate. The solution is then crystallized by concentration such that sodium sulfate and impurities are precipitated, with the generated sodium sulfate acting indirectly as a filter aid. This achieves the purpose of rapid separation and facilitates the embodiment of industrialization.

Based on the present disclosure, applying the impurity-removal and mother liquor recovery in an ethylene oxide production process for taurine comprises the following steps:

S1. ethylene oxide reacts with sodium hydrogen sulfite solution to generate sodium isethionate;

S2. sodium isethionate generated in S1, the recycled mother liquor after treatment, and ammonia (e.g., ammonia water) are mixed to generate the reaction liquid, and then ammonia is absorbed to a certain degree of concentration, and an aminolysis reaction is carried out under the action of a catalyst, and the sodium taurate solution is generated by evaporation and concentration;

S3. a taurine solution is generated from the sodium taurate solution generated in S2 using an acidic cation exchange resin; alternatively, an acid such as sulfuric acid is added to neutralize to pH 7.0-8.5 such that a taurine crystallization solution is obtained;

S4. the taurine solution generated by using an acidic cation exchange resin is concentrated and crystallized to generate the crude taurine and mother liquor, and the (first) crude taurine is removed from the (first) mother liquor; when S3 used an acid such as sulfuric acid to generate solid taurine in the crystallization solution, the crude taurine is separated from the first mother liquor after cooling and crystallizing; in either instance, the mother liquor is then concentrated and crystallized several times, with taurine separated and extracted each time, and the remaining liquid concentrated to generate the last mother liquor of taurine;

S5. add a certain amount of alkali to the last mother liquor of taurine collected in S4, and stir it evenly, preferably liquid alkali. A certain amount of acid is then added to achieve a pH value of 7.0-10.5, and the reaction temperature is controlled from 50° C. to 75° C. In one specific embodiment, the acid is sulfuric acid, and the pH value is adjusted to 8.5-10, or 9.0-9.5.

S6. transfer the material collected in S5 to a concentrator system for concentration, such that 30-60% or 35%-45% of the water is evaporated, and the solution is concentrated about 1.4-2.5 times or 1.5-1.8 times, thereby generating a crystallization solution. In one particular embodiment, the water is evaporated by 40%-42%, and the concentration ratio is from 1.65 to 1.72 times.

S7. transfer the material collected in S6 to a cooling crystallization tank, and cool to 65-99° C., or 72-78° C., and then filter using a plate and frame device (or using another type of filtration device) to generate a clear solution.

S8. the solution collected in S7 is cooled to 15-25° C., or 18-22° C., and then a certain amount of activated carbon is added, and liquid alkali is added to achieve a pH value of 9.0-10.5, or 9.5-10, and then the solutions is passed through a plate and frame filtration device, a micropore filter or other type of filtration device to separate the mother liquor.

S9. liquid ammonia or ammonia is added to the mother liquor collected in S8 under cooling conditions to achieve a mass to volume ratio of ammonia greater than 15 g/100 ml (15%), or 17-19 g/100 ml (17-19%)), such that a large amount of salt and other impurities will be precipitated; the solution is then filtered (e.g., with a vane filter or a sealed plate filter) to generate a clear mother liquid, and the generated mother liquid can be returned to step S2 for use in the aminolysis step.

It should be noted that the sodium isethionate generated in S1 can be concentrated and crystallized and dried to generate the corresponding solid, or the mixed liquid generated by the reaction can be directly mixed with the ammonia in S2 without treatment after the direct reaction of S1is completed. In one embodiment, the ammonia concentration in the reaction solution in S2 after ammonia absorption is 20-28 wt % (weight percent).

In one embodiment, the concentration of the sodium hydrogen sulfite solution in S1 is 9-36 wt %, and the ratio of the amount of sodium hydrogen sulfite to ethylene oxide is 1:0.95-1.

In one embodiment, the catalyst used in S2 is any one of sodium hydroxide, potassium hydroxide, lithium hydroxide, sodium carbonate, potassium carbonate, lithium carbonate, or a mixture of two or more of the foregoing, and the temperature of the aminolysis reaction is 150-290° C., and the pressure in S2 is 10-25 MPa. Preferably, the alkali added in S5 is the same as the catalyst used in S2, avoiding new impurities being generated.

In one embodiment, when the sodium taurate is treated with the acidic cation exchange resin column in S3, the concentration of the sodium taurate solution is 15%-35%, or 18%-20%. When sodium taurate is treated with sulfuric acid in S3, the concentration of sodium taurate solution is 25%-40%, or 32%-38%.

To produce finished taurine, the crude taurine recovered in S4 is dissolved in water, activated carbon added, etc., then decolorized and filtered, cooled and crystallized, and dried after centrifugation to generate the finished taurine. The fine mother liquor after centrifugation can be reused in the preparation of sodium taurate solution or taurine decolorization ingredients.

In S4, after the initial removal of the first crude taurine from the taurine solution of S3, the mother liquor is concentrated and crystallized several times. For example, the mother liquor can be concentrated once or twice, respectively, to generate the second or third crude products (taurine) and the second or third mother liquors, respectively. When S3 uses an acidic cation exchange resin column for the treatment of sodium taurate, it is preferred that the last mother liquor of taurine is the second mother liquor; when S3 uses sulfuric acid to treat sodium taurate, the preferred last mother liquor is the third mother liquor.

By applying the methods of the present disclosure, a production system for fully recovering and treating the taurine mother liquor is provided, which reduces the filtration resistance of the last mother liquor by a pretreatment system comprising a reaction device and/or a concentration device connected in series, a cooling and crystallization device and a first filtration device.

In one embodiment, the discharge port of the pretreatment system is connected to an activated carbon decolorization and impurity removing device, and the activated carbon decolorization and impurity removing device comprises a decolorization tank and a second filter device, and the decolorization tank is equipped with a feed port for adding activated carbon and alkali. There is also a cooling mechanism for reducing the temperature inside the tank.

In one particular embodiment, the activated carbon decolorization and impurity removing device comprises a decolorization tank, an inlet frame filter pump, a plate and frame filter, a transfer tank, a precision filtration pump, a precision filter and a receiving storage tank which are sequentially connected.

The discharge port of the activated carbon decolorization and impurity removing device can be connected to an ammonia-mixing desalination device, wherein the ammonia-mixing desalination device includes an ammonia-mixing reaction tank and a closed filtration device provided with a circulation passage.

In one particular embodiment, the ammonia-mixing reaction tank is equipped with an ammonia inlet, a feed port and a discharge port, and the discharge port of the ammonia-mixing reaction tank is connected to a feed port of the closed filtration device by a pump, and the pump is equipped with a rotary discharge valve for discharging the filtered clear material.

In one particular embodiment, the first filtration device is a plate and frame filter.

In some embodiments, the reaction device and the temperature-lowering crystallizer slurry device of the pretreatment system are respectively equipped with a temperature lowering mechanism for lowering the temperature inside the respective tanks of these devices.

The temperature lowering mechanism can be an externally disposed water circulation condensation layer, and the condensation layer is provided with a cooling water inlet valve and a cooling water outlet valve.

Embodiments of the methods and systems of the present disclosure provide one or more of the following advantages and beneficial effects:

1. According one embodiment of the methods and systems of the present disclosure, the salt is added to the last mother liquor of taurine, or the last mother liquor of taurine is treated with alkali and acid to realize the phenomenon that impurities are precipitated at different temperatures, concentrations and pH, and the active ingredient (taurine) is not precipitated. Furthermore, the added or generated salt forms a bridge with the precipitated impurities, reduces the filtration resistance, and also reduces the viscosity of the mother liquor, solving the problem of separating impurities, greatly shortening the time of impurity removal, and thus removing effectively more impurities in the mother liquor, and further removing the salt by ammonia-mixing treatment to obtain the pure taurine mother liquor, thereby realizing recovery of the mother liquor to improve product yield.

2. The activated carbon decolorization and impurity removing device used in the present disclosure is operated under the condition of cooling, and the activated carbon adsorbs a certain amount of impurities such as ethylene glycol, metal ions and a small amount of organic substances, so that the impurities in the taurine mother liquor are removed more thoroughly.

3. Embodiments of the impurity recovery production system of the present disclosure adopt an optimized design and utilize an effective removing impurity device to remove all kinds of impurities contained in the last mother liquor. It is efficient, complete, simple in operation and low in operation cost.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

Figure 1:
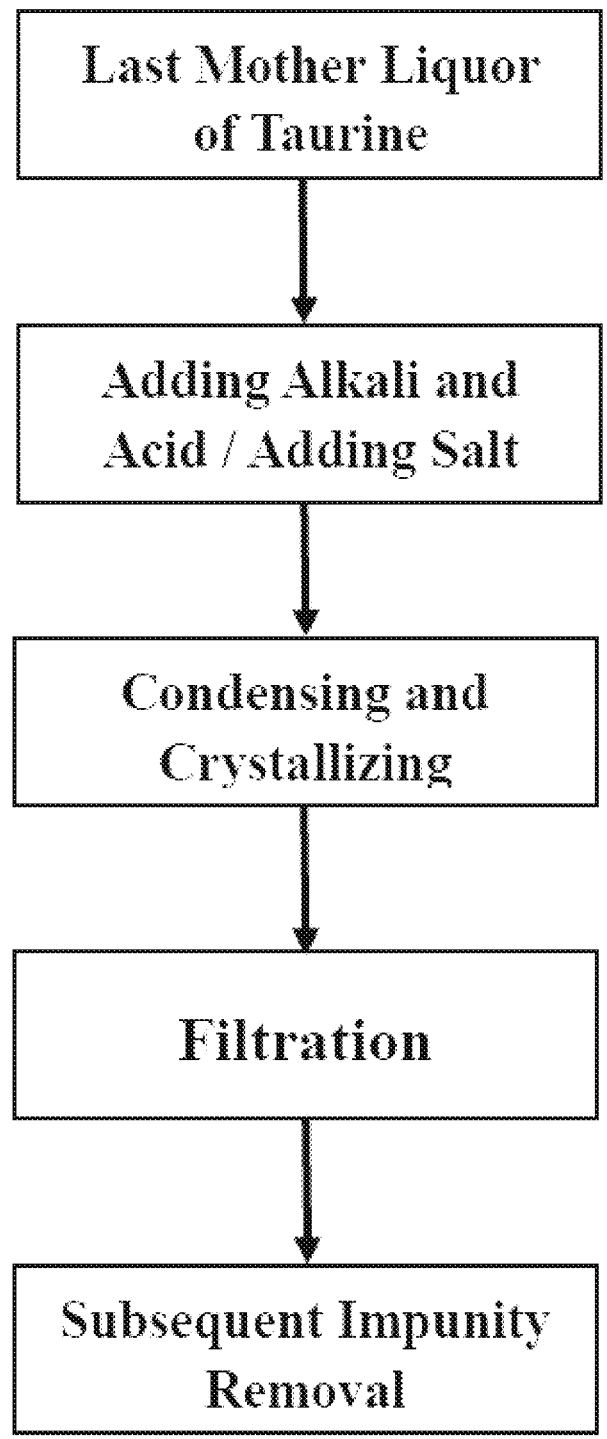
FIG. 1: A process flow chart of the last mother liquor pretreatment of an embodiment of the present disclosure.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

As shown in FIG. 1, the present disclosure provides a method for removing impurities from and recycling the taurine mother liquor and adding a pretreatment process to the last mother liquor treatment in the existing ethylene oxide process for producing taurine. In particular, alkali and acid are added sequentially to the last mother liquor of taurine, and then it is concentrated, crystallized and filtered. The viscosity of the last mother liquor is reduced firstly to generate the transparent last mother liquor of taurine, and then subjected to subsequent decolorization and impurity removal treatment, so that the treated last mother liquor can be recycled and utilized efficiently.

Figure 2:
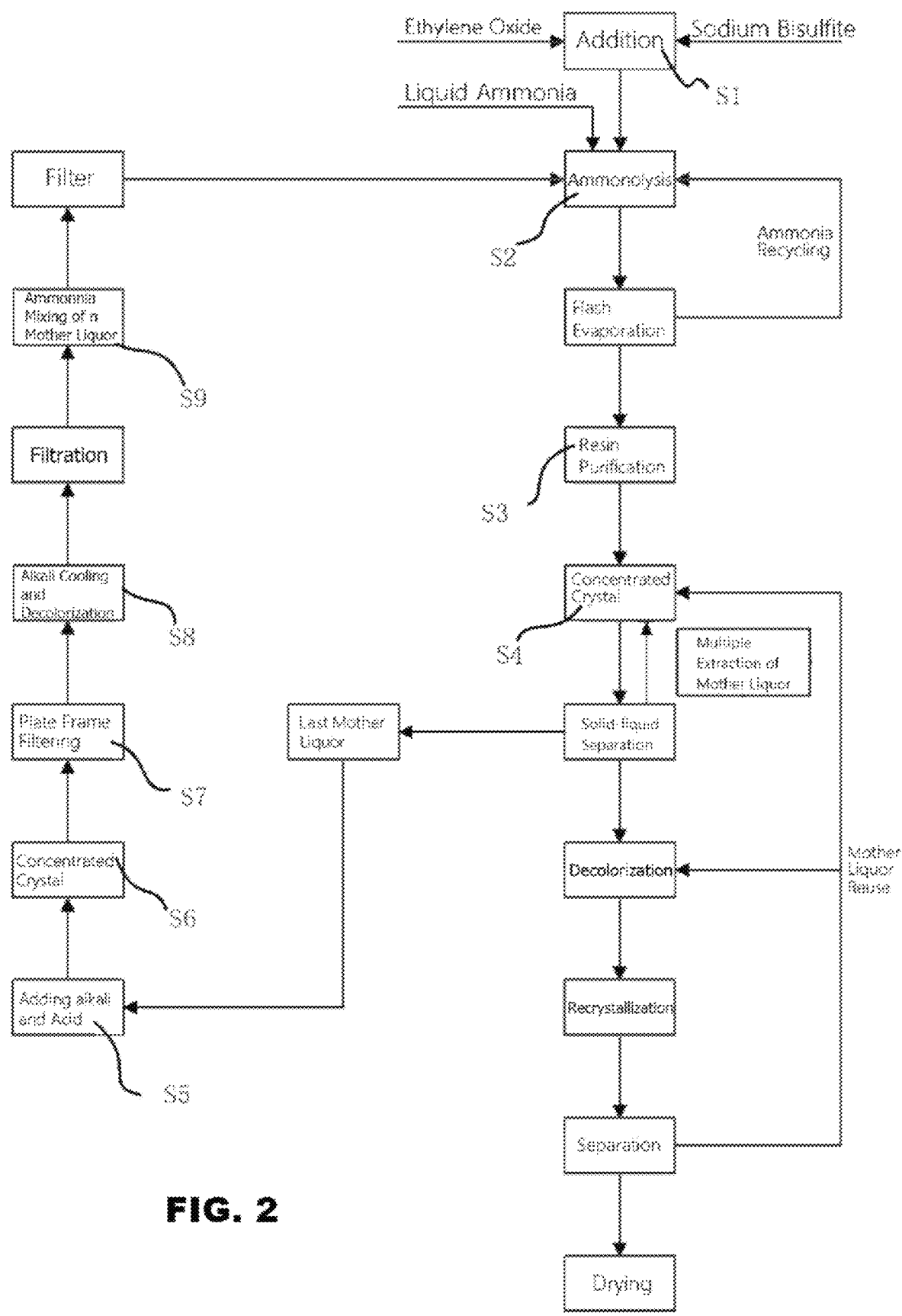
FIG. 2: A process flow chart for producing taurine by the ethylene oxide method using an embodiment of the present disclosure, wherein a cation exchange resin is used to generate the taurine solution and the decolorization and removing impurities with the activated carbon and the ammonia-mixing treatment are performed after the pretreatment.
Figure 3:
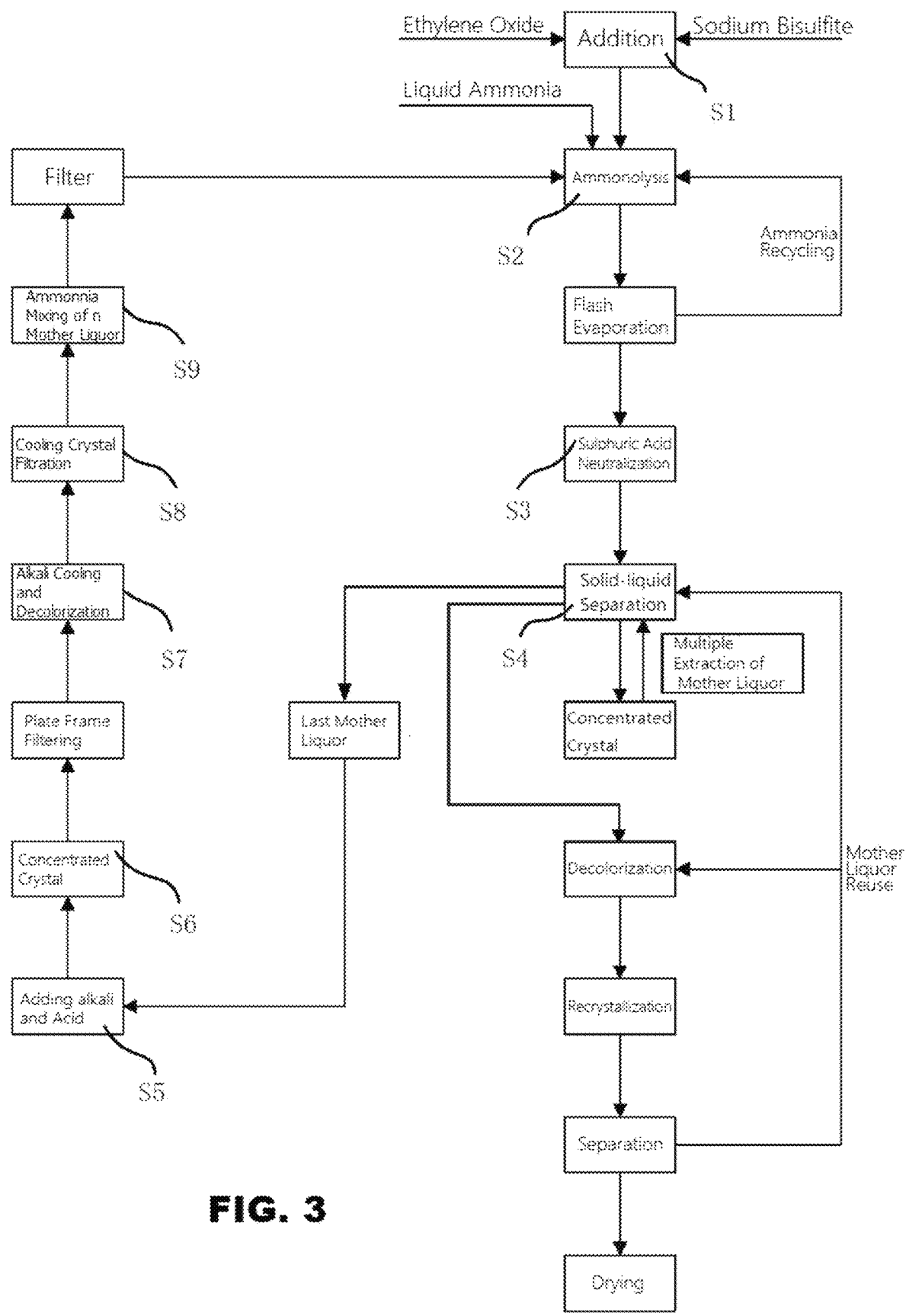
FIG. 3: A process flow chart for producing taurine by the ethylene oxide method using an embodiment of the present disclosure, wherein sulfuric acid is used to generate the taurine solution and the decolorization and removing impurities with the activated carbon and the ammonia-mixing treatment are performed after the pretreatment.

As shown in FIGS. 2 and 3, the pretreatment process can be applied to the process of preparing taurine by an ethylene oxide process, with the following steps.

S1. ethylene oxide reacts with sodium hydrogen sulfite (sodium bisulfite) solution to generate sodium isethionate; in this step, impurities such as ethylene glycol and polyethylene glycol are generated.

S2. sodium isethionate generated in S1, recycled mother liquor after impurity removal treatment, and ammonia (e.g., ammonia water) are mixed to generate the reaction solution, and then ammonia is absorbed to a certain concentration, and the aminolysis reaction is carried out under the action of catalyst. After the reaction is completed, flash evaporation is performed to discharge excessive ammonia from the reaction solution, and the discharged ammonia is recycled and utilized as a raw material for aminolysis reaction. Following the discharge of excessive ammonia, the solution is concentrated by evaporation to generate the sodium taurate solution at the desired concentration. The ethylene glycol by-product in the sodium isethionate solution produced in step S1 is converted into organic impurities such as polyether alcohols. Since the aminolysis reaction is a reversible reaction, according to the chemical equilibrium theory, the presence of sodium ditaurate or sodium tritaurate can achieve the purpose of improving the conversion rate of the raw material. The mother liquor after the impurity removal treatment can reach the purpose of increasing the application of the liquid and reducing the side reactions, thereby fulfilling the purpose of stabilizing production and improving yield further. When the sodium taurate is treated with an acidic cation exchange resin column in S3, the concentration of the sodium taurate solution is adjusted to 15%-35%, or 18%-20%. When the sodium taurate is treated with sulfuric acid in S3, the concentration of the sodium taurate solution is adjusted to 25%-40%, or 32%-38%.

S3. the sodium taurate solution generated in S2 is prepared at a certain concentration, and a slurry of taurine is generated by either: (a) mixing through the acidic cation exchange resin column; or (b) using a sulfuric acid neutralization process, reaching a pH value of 7.0-8.5 by adding sulfuric acid to generate a taurine crystal solution.

S4. when S3 uses an acidic cation exchange resin, the slurry of taurine is concentrated and crystallized, followed by separation of crude taurine from the mother liquor at a separation temperature of about 25° C.; when S3 uses a sulfuric acid neutralization process, the slurry of taurine is cooled and crystallized, followed by separation of crude taurine from the mother liquor at a separation temperature of about 32° C.-35° C.; thereafter, in either instance the mother liquor is further concentrated (water evaporated), cooled, and crystallized one or more times, and additional crude taurine separated and extracted each time by means of a plate and frame filter or other filtration device; finally, the last mother liquor of taurine is concentrated.

S5. liquid sodium hydroxide (e.g., 5-50% by volume) is added to the last mother liquor of taurine collected in S4 and the mixture is stirred evenly. A certain amount of sulfuric acid is then added thereto to reach a pH value of 7.0-10.5, and the reaction temperature is controlled at 50° C.-95° C. The substance in the solution (mainly sodium taurine, sodium hydroxyethyl sulfonate, and sodium iminodiethylsulfonate) is present in the form of a sodium salt firstly, and then sodium sulfate is formed when sulfuric acid is added.

S6. transfer the solution from S5 to a concentrator system for concentration, whereby the water is concentrated and evaporated by 30%-60%, and the times of concentration is about 1.4-2.5. The concentration times and the concentration temperature can be controlled to generate the best crystallization effect, and to precipitate impurities and sodium sulfate.

S7. transfer the solution obtained in S6 to the cooling crystallization tank and cool down to 65-99° C. and keep the temperature in this range. The solubility of sodium sulfate will increase with the decrease of temperature, and the solubility of taurine will increase with the increase of temperature. This temperature will ensure that the impurities and sodium sulfate reach a certain ratio, such that the taurine will not precipitate. The high temperature also reduces the viscosity of the solution, because a certain amount of sodium sulfate crystals exist in the impurities, forming the filter bridge, facilitating the separation of impurities. The solution then enters the plate and frame filtering device, which enables fast separation.

S8. the solution collected in S7 is cooled to 15-25° C., a certain amount of activated carbon is added, liquid alkali is added to adjust the pH to 9.0-10.5, and the mother liquor is separated by a filter device such as a plate and frame or microporous filter;

S9. add liquid ammonia into the taurine mother liquor, which is cleaned of impurities thoroughly collected in S8 under the cooling condition, until the ammonia content is at least 15%. A large amount of sulfate and other impurities will be precipitated, and then a blade filter or a sealed plate and frame filter is used. The clear mother liquor is filtered, and the generated mother liquor can be recycled to the aminolysis step (S2 step). The filter device be sealed to prevent leakage of ammonia and to comply with environmental protection requirements.

In order to explain the technical effects of this invention, several examples are described below. All of the raw materials used in the following examples were commercially available unless otherwise specified. The methods were conventional unless otherwise specified, and the content of the materials refers to the mass percentage by volume unless otherwise specified.

Example 1

In this example, the last mother liquor of taurine is treated with alkali and acid, and is decolorized and removed of impurity by activated carbon:

(1) The last mother liquor of taurine: 1500 ml of taurine mother liquor, wherein the mass percentage of taurine is 10% (based on taurine, 100 ml solution contains 10 g of taurine), and 375 ml of liquid sodium hydroxide concentration of 32% is added and stirred well, and then 100 ml of concentrated sulfuric acid with a concentration of 98% is added, and the reaction temperature is controlled at 50-75° C.

(2) The solution is then concentrated to 1185 ml by evaporation, and the concentrated liquor is subjected to suction filtration at 75° C. for 15 minutes. After filtration, 975 ml of the filtrate and 510 g of the solid is generated. The solid is relatively dry and the share of water is 15%.

(3) 46 ml of liquid sodium hydroxide with concentration of 32% is added to the filtrate, and the temperature is lowered to 18-22° C. Then, 1 g of activated carbon is added thereto. After stirring for a certain period of time, 970 ml of the mother liquid is generated by suction filtration. The main components in the mother liquid are taurine and sodium isethionate. The testing content of taurine is 15.2% and the content of sodium isethionate is 18.2%. Compared with the last mother liquor of taurine before treatment, the content of taurine and sodium isethionate is obviously increased, and the content of impurities such as ethylene glycol and Fe are significantly reduced.

The testing data is as follows:

| Item | The last mother liquor of taurine (before treatment) | The last mother liquor of taurine (after treatment) |
| --- | --- | --- |
| Ethylene Glycol | 6% | 0.5% |
| Fe | 10 ppm | <1 ppm |
| Content of Taurine | 10% | 15.2% |
| Content of Sodium Isethionate | 12% | 18.2% |
| Outer Appearance | Yellow | Light Yellow |

Example 2

This example shows the control process experiment of the last mother liquor of taurine:

(1) The last mother liquor of taurine: 1500 ml of taurine mother liquor, containing 10% by mass of taurine (based on taurine, 10 g of taurine in 100 ml of solution). The solution is concentrated to 1185 ml, and then suction filtered at 75° C. When the filtration time is 3 hours, the solid matter generated by suction filtration is thinner, more viscous, with more water (moisture content is 30% by mass) as compared to Example 1; the suction filtration effect is not as good as Example 1, requiring suction filter equipment of more power, higher energy consumption and lower efficiency.

(2) The last mother liquor of taurine: 1500 ml of taurine mother liquor, containing 10% by mass of taurine (calculated as taurine, 10 g of taurine in 100 ml of solution), was concentrated to 1185 ml. The concentrated liquor was separated at 75° C. by a centrifuge for 15 minutes, and the solid generated by centrifugation is relatively thinner, more viscous, with more water (moisture content is 28% by mass) as compared to Example 1, mainly due to the higher viscous concentrate. The viscosity is higher and the separation effect is poor.

Example 3

Conduct ammonia-mixing treatment to the last mother liquor in Example 1 and recover it.

The ammonia-mixing treatment of the recovered mother liquid: the mother liquid collected in Example 1 is injected with liquid ammonia to reach an ammonia content of 15%-20% and filtered to obtain a transparent clear solution.

Preparation of sodium taurine: with the catalyst present as sodium hydroxide, a sodium isethionate solution (manufactured by the Applicant), the ammonia-mixing treated mother liquor (from the previous step) and ammonia gas are subjected to an aminolysis reaction. The aminolysis reaction is carried out at 220-280° C. and 10-15 MPa. The reaction is carried out for 1 hour. After the reaction is completed, the solution generated by flashing off the ammonia gas is the sodium taurate solution.

Through testing, the treated mother liquor is substantially free of sulfate.

Example 4

Conduct directly ammonia-mixing treatment on the last mother liquor without the treatment in Example 1, and the step S7 is performed for recycling.

The ammonia-mixing treatment of the recovered mother liquor: the raw material used in Example 1 (i.e., the last mother liquor, but without being subjected to the treatment with alkali and acid) was combined with liquid ammonia to reach an ammonia content of 15%-20% and was then filtered to obtain a clear solution.

Preparation of sodium taurate: with the catalyst present as sodium hydroxide, a sodium isethionate solution (manufactured by the Applicant), the ammonia-mixing treated mother liquor (from the previous step) and ammonia gas are subjected to an aminolysis reaction. The aminolysis reaction is carried out at 220-280° C. and 10-15 MPa for 1 hour. After the reaction is completed, the solution generated by flashing off the ammonia gas is the sodium taurate solution.

Example 5

Two sets of experiments according to the present disclosure and corresponding comparative experiments were selected to show the situation of aminolysis and the subsequent extraction of crude taurine under various conditions of mother liquor reuse.

All of the following experiments used 1.5 moles of sodium isethionate, and the sodium taurate solution was prepared according to the methods of Examples 3 and 4. The generated sodium taurate solution was treated with a cation exchange resin to obtain taurine. The resulting taurine solution was concentrated, cooled and crystallized to obtain a crude taurine, and the content of taurine was measured.

The yield ratio was calculated according to the following formula:

$$\text{Aminolysis yield ratio} = \text{the mass of pure taurine} \div (\text{Mass of sodium isethionate} \div 148 \times 125) \times 100\%.$$

The results are shown in the table below

| SN of Experiment | Item | Mother Liquor | | | | Sodium taurate solution | Aminolysis yield ratio Calculating | Crude taurine | |
|---|---|---|---|---|---|---|---|---|---|
| | | Volume ml | Taurine content (g/ml) | Sodium isethionate content (g/ml) | Sodium isethionate Mass (g) | The quality of pure taurine (g) | by the sodium isethionate input | Mass (g) | Content (g/g) |
| 1 | Example 4 | 115 | 10% | 12% | 222 | 172.5 | 92.00% | 162.7 | 88% |
| 2 | Example 4 | 135 | 10% | 12% | 222 | 177.2 | 94.50% | 171 | 86% |
| 3 | Example 3 | 75 | 15.20% | 18.20% | 222 | 188.44 | 100.00% | 173.2 | 93.10% |
| 4 | Example 3 | 90 | 15.20% | 18.20% | 222 | 206.63 | 110.00% | 188.5 | 93.20% |

By comparing Experiment 3 and Experiment 4 of Example 5, it is seen that the increased dosage of the treated mother liquor increases the yield of the aminolysis reaction, while the crude product content is not affected, and the mother liquor impurities after the counter-treatment would be less.

Comparing Experiment 1 and Experiment 3 of Example 5, and comparing Experiment 2 with Experiment 4 of Example 5, it is seen that the amount of mother liquor before and after treatment is the same under the same conditions (the same amount of purity), the yield of aminolysis reaction increases significantly, and the content of the crude product is significantly improved, which fully demonstrates that the mother liquor is more thoroughly reduced after the treatment according to the present disclosure, so that the side reaction under the aminolysis reaction condition is greatly reduced, and the product quality is greatly improved.

Comparing Experiments 1, 2, 3, and 4 of Embodiment 5 overall, the effective content of the mother liquor after treatment is greatly improved, and, at the same time, the yield is improved and the crude product content is increased, and, at the same time, the amount of mother liquor recycled can be increases after the treatment (under the situation that the pureness is equivalent).

Example 6

In this example, salting treatment and activated carbon decolorization and impurity removal treatment are conducted on the last mother liquor of taurine:

(1) The last mother liquor of taurine: 1500 ml of taurine mother liquor, containing 10% by mass taurine (calculating according to taurine, 10 g of taurine in 100 ml of solution), and 127.8 g of $Na_2SO_4$ salt (i.e. 0.9 mol) are combined and the solution is stirred evenly, with the temperature controlled at 50-75° C.

(2) The solution is then concentrated to 1185 ml (by evaporation), and the concentrated liquor is suction filtered at 75° C. for 15 minutes. After filtration, 1050 ml of the filtrate and 210 g of the solid were generated. The solid is relatively dry and the share of water is 23%.

(3) 50 ml of liquid sodium hydroxide with a concentration of 32% is added to the filtrate, and the temperature is lowered to 18-22° C. Then, 1 g of activated carbon is added thereto. After stirring for a certain period of time, 1046 ml of the mother liquid is generated by suction filtration. The main components in the mother liquid are taurine and sodium isethionate. The testing content of taurine is 13.8% and the content of sodium isethionate is 16.5%. Compared with the last mother liquor of taurine before treatment, the content of taurine and sodium isethionate is obviously increased, and the content of impurities such as ethylene glycol and Fe are significantly reduced.

The testing data is as follows:

| Item | The last mother liquor of taurine (before treatment) | The last mother liquor of taurine (after treatment) |
| --- | --- | --- |
| Ethylene Glycol | 6% | 0.8% |
| Fe | 10 ppm | <1 ppm |
| Content of Taurine | 10% | 13.8% |
| Content of Sodium Isethionate | 12% | 16.5% |
| Outer Appearance | Yellow | Light Yellow |

Example 7

In this example, salting treatment and activated carbon decolorization and impurity removal treatment is conducted on the last mother liquor of taurine:

(1) The last mother liquor of taurine: 1500 ml of taurine mother liquor, wherein the mass percentage of taurine is 10% (calculating according to taurine, 100 ml solution contains 10 g of taurine), and 568 g of $Na_2SO_4$ salt is added thereto (i.e. 4 mol) are combined and the solution is stirred evenly, with the temperature controlled at 50-75° C.

(2) The solution is then concentrated to 1185 ml, and the concentrated liquor is suction filtered at 75° C. for 15 minutes. After filtration, 985 ml of the filtrate and 774 g of the solid were generated. The solid is relatively dry and the share of water is 15%.

(3) 47 ml of a liquid sodium hydroxide with a concentration of 32% is added to the said filtrate, and the temperature is lowered to 18-22° C. Then, 1 g of activated carbon is added thereto. After stirring for a certain period of time, 980 ml of the mother liquid is generated by suction filtration. The main components in the mother liquid are taurine and sodium isethionate. The testing content of taurine is 14.8% and the content of sodium isethionate is 17.8%. Compared with the last mother liquor of taurine before treatment, the content of taurine and sodium isethionate is obviously increased, and the content of impurities such as ethylene glycol and Fe are significantly reduced.

The testing data is as follows:

| Item | The last mother liquor of taurine (before treatment) | The last mother liquor of taurine (after treatment) |
| --- | --- | --- |
| Ethylene glycol | 6% | 0.6% |
| Fe | 10 ppm | <1 ppm |
| Content of Taurine | 10% | 14.8% |
| Content of Sodium Isethionate | 12% | 17.8% |
| Outer Appearance | Yellow | Light Yellow |

Exemplary processing equipment of the present disclosure will be described in detail below with reference to the drawings.

Figure 4:
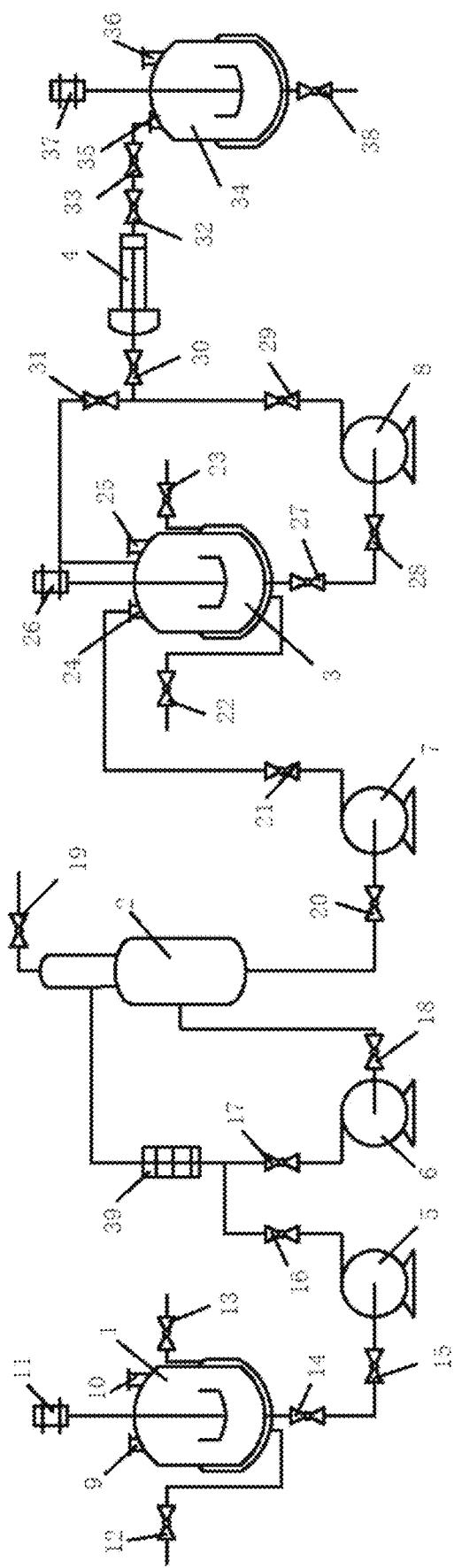
FIG. 4: A schematic diagram of a mother liquor pretreatment system according to one embodiment of the present disclosure.

As shown in FIG. 4, the present disclosure provides a pretreatment system for removing the impurities from and recycling taurine mother liquor (e.g., utilizing the impurity removal and recovery method shown in FIG. 1). The pretreatment system comprises, sequentially, a tank 1 for adding alkali and acid to the last mother liquor, a concentration tank 2, a concentrated discharge crystallizer slurry tank 3, a filter device 4 (e.g., a plate and frame filtration device), and an intermediate transfer tank 34. These components are connected, and the necessary equipment such as pumps are connected between these components. The concentrator tank 2 is connected with a heat exchanger 39, and cooling mechanisms are provided for the alkali and acid addition tank 1 and the concentrated discharge crystallizer tank 3 for reducing the temperature of the material in these tanks. Among them, the alkali and acid addition tank 1, the concentrated discharge crystal slurry tank 3 and the intermediate transfer tank 34 can all be ordinary pressure vessels.

The feed port 9 of the alkali and acid addition tank 1 can be connected to the discharge port of the device generating the last mother liquor of taurine. The mother liquid feed port 9, an exhaust port 10 and a stirring mechanism 11 are installed on the alkali and acid addition tank 1. A discharge valve 14 is arranged below the alkali and acid addition tank 1. A water circulation condensation layer, also referred to as a water jacket, is arranged on the outside the alkali and acid addition tank 1 for reducing the temperature in the alkali and acid addition tank 1. This water circulation condensation layer or water jacket is provided with a cooling water inlet valve 12 and a cooling water outlet valve 13. Raw material pumps 5 and 6 are located between the concentration tank 2 and the acid and alkali addition tank 1. Raw material pump 5 is equipped with feed valve 15 and discharge valve 16, and raw material pump 6 is equipped with feed valve 17 and discharge valve 18. The discharge valve 16 and feed valve 17 are connected to a heat exchanger 39. Above the concentration tank 2, a vent valve 19 (valve normally open) is provided, and the lower part of the concentration tank 2 is connected to a raw material pump 7. The raw material pump 7 is provided with a feed valve 20 and a discharge valve 21. The discharge valve 21 is connected with the feed port 24 of the concentrated discharge crystallizer tank 3. The mother liquor feed port 24, as well as a vent port 25 and a stirring device 26 are provided at the top of the concentrated discharge crystallizer tank 3, and a discharge valve 27 is installed below. A water jacket is equipped on the outer shell of the concentrated discharge crystallizer slurry tank 3 to lower the temperature in the tank. Cooling water inlet and outlet valves 22 and 23 are also provided. The discharge valve 27 is in fluid communication with a plate and frame filter pump 8 through a feed valve 28. A discharge valve 29 and a reflux valve 31 are provided in fluid communication with the plate and frame filter pump 8. A plate and frame filter device 4 is provided, along with a feed valve 30 and a discharge valve 32 in fluid communication with the filter device 4. The fluid discharge of the filter device 4 is in fluid communication with the transfer tank 34, through the feed valve 33. A feed port 35, vent port 36 and stirring device 37 are installed on the top of transfer tank 34, and a bottom discharge valve 38 at the bottom of the tank 34 is connected with the subsequent equipment shown in FIG. 5 (and described below). Apart from the pipeline valves, there are some additional necessary valves and connecting parts for the system that are not shown. These can be common devices and apparatus and are not described in detail herein.

Figure 5:
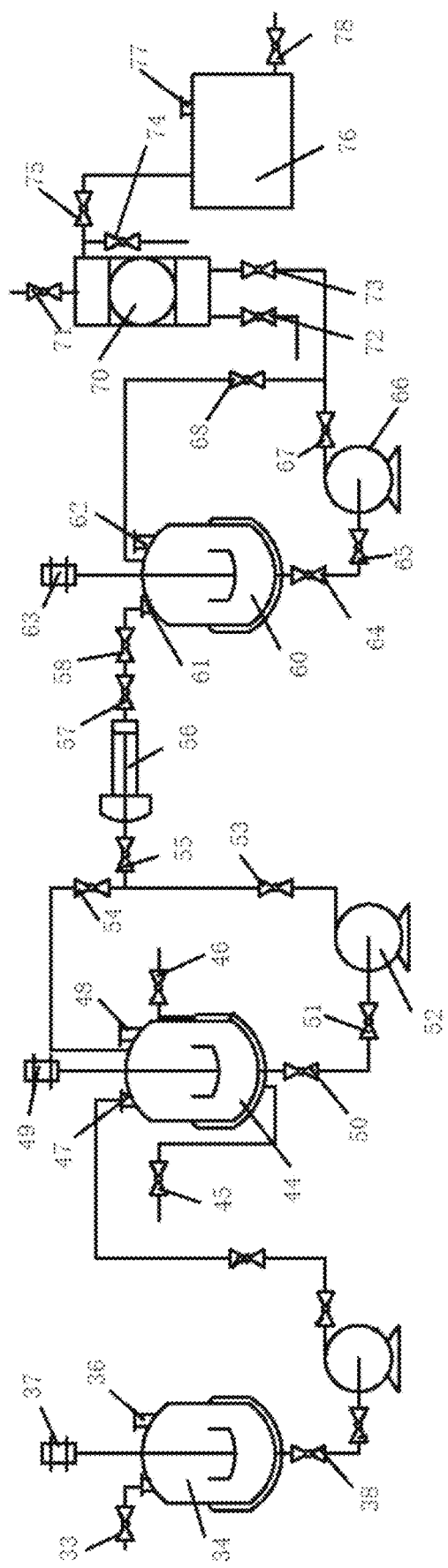
FIG. 5: A schematic diagram of an activated carbon decolorization and impurity removing system according to one embodiment of the present disclosure, wherein a portion of the system of FIG. 4 is included for point of reference.

FIG. 5 displays an embodiment of the subsequent system for impurity-removal, namely for the material flowing out of transfer tank 34 entering into the activated carbon decolorization and impurity removal system. In other words, the last mother liquor of taurine generated by the pretreatment in the system of FIG. 4 is subjected to decolorization and impurity removal by activated carbon in the system of FIG. 5. Specifically, the activated carbon decolorizing and impurity removal system includes a decolorization tank 44, a filter inlet pump 52, a plate and frame filter 56, a transit tank 60, a precision filter pump 66, a precision filter 70, and a receiving storage tank 76, which are sequentially connected. The precision filter 70 has a smaller filter pore size than the plate and frame filter 56 and can filter out smaller particle impurities. Among them, the decolorization tank 44, the intermediate tank 60 and the receiving storage tank 76 are all ordinary pressure equipment.

The exterior shell of the decolorization tank 44 is equipped with a water circulation condensation layer (or water jacket) for reducing the temperature inside the decolorization tank 44. The water circulation condensation layer is provided with a cooling water inlet valve 45 and a cooling water outlet valve 46. The decolorization tank 44 is equipped with a stirring mechanism 49, and the upper portion of the tank 44 is equipped with a mother liquid feeding port 47 and an exhaust port 48. The tank 44 is provided with a discharge valve 50 at the bottom. The discharge valve 50 is connected with the plate and frame filter inlet pump 52 through the feeding valve 51 of the filter inlet pump 52, and the plate and frame filter inlet pump 52 is provided with a discharge valve 53 and a return valve 54. The inlet and outlet of the plate and frame filter 56 are respectively provided with a feed valve 55 and a discharge valve 57, and the latter is connected to the intermediate transit tank 60 through a feed tank inlet valve 58. A feed port 61, a port 62 and an agitation mechanism 63 are installed above the transit tank 60. A bottom discharge valve 64 is connected to the precision filter pump feed valve 65; the outlet end of the precision filter pump 66 is connected to the discharge valve 67, and connects with the precision filter pump return valve 68 and precision filter feed valve 73. The precision filter 70 is equipped with a cleaning water inlet valve 71, a cleaning water outlet valve 72 and an exhaust valve 74. The discharge valve 75 of the precision filter 70 is connected to the inlet of the receiving storage tank 76. The receiving storage tank 76 is equipped with an exhaust port 77, and its discharge valve 78 is connected to the subsequent devices. Other valves and connecting components necessary for the manufacturing equipment are common technical means in the art and will not be described herein. A liquid feed port is preferably installed on the decolorization tank for adding and filling the liquid sodium hydroxide or the liquid acid.

With the system of FIG. 5, the filtration efficiency and the processing capacity can be improved by two-stage filtration. In operation of the system of FIG. 5, activated carbon is added to the decolorization tank from the mother liquid feeding port 47, and can also be added from other openings, which is not limited. The discharge valve 50 of the decolorization tank is closed, and the material from the intermediate transfer tank 34 is added to the decolorization tank 44 through feed port 47 of the decolorization tank. The cooling water outlet valve 46 and the cooling water inlet valve 45 are opened such that the temperature within the decolorization tank is lowered by the cooling water. Meanwhile, the decolorizer stirring mechanism 49 is started. After the temperature is lowered to the predetermined temperature, the cooling water inlet valve 45 and the cooling water outlet valve 46 are closed. The decolorizer discharge valve 50, the inlet frame filter pump feed valve 51, the plate and frame feed valve 55, the plate and frame discharge valve 57 and the transit tank feed valve 58 are opened, the transit tank discharge valve 64 is closed, the plate and frame filter pump 52 is started, and the pressure of the plate and frame filter is adjusted using the plate and frame filter pump return valve 54. The activated carbon and the mother liquor are introduced into the plate and frame filter 56, and the activated carbon is trapped in the filter 56; the plate and frame filter can be opened in order to discharge the activated carbon that has adsorbed impurities. After the material of the transit tank 60 reaches a certain volume, the transit tank discharge valve 64, the precision filter pump feed valve 65, the precision filter pump return valve 68, the precision filter feed valve 73, the precision filter exhaust valve 74 and the precision filter discharge valve 75 are opened, the precision filter pump 66 is launched, and the precision filter pump discharge valve 67 is opened. After the precision filter exhaust valve 74 is discharged, the precision filter exhaust valve 74 is closed. The feed pressure of the precision filter 70 is adjusted by the precision filter pump return valve 68. The material collected by the receiving tank 76 is sent to a subsequent section for processing.

Figure 6:
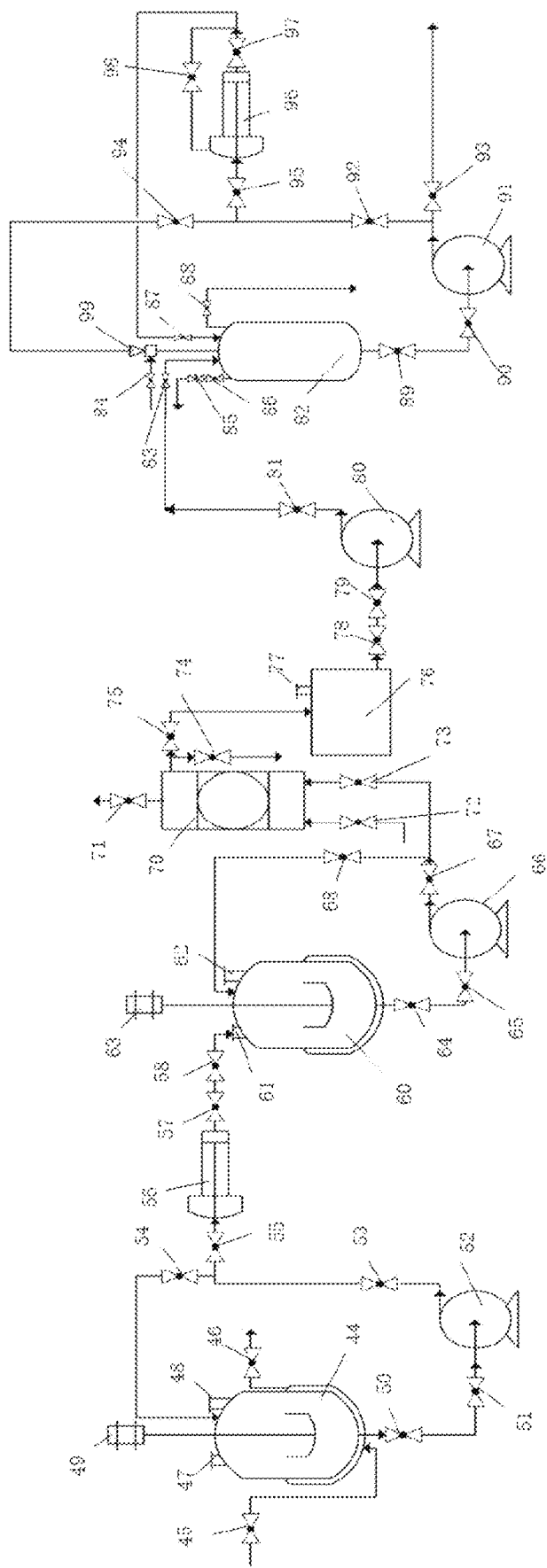
FIG. 6: A schematic diagram of an ammonia-mixing and desalination system according to one embodiment of the present disclosure, wherein a portion of the system of FIG. 5 is included for point of reference.

The embodiment shown in FIG. 6 optimizes the process and equipment, and comprises an activated carbon decolorization and impurity removal system and an ammonia-mixing and desalination system. The ammonia-mixing and desalination system includes a flow-through ammonia-mixing reaction tank 82, pump 91, and vane filter 96, which are sequentially connected. The vane filter 96 can also be replaced with a sealed plate and frame filter. An ammonia aspirator 99, ammonia inlet valve 84, feed valve 83, clear liquid return valve 87 emptying valve 88, safety valve 86, and safety valve front control valve 85 are equipped above the ammonia-mixing reaction tank 82. The ammonia reaction is carried out within the ammonia-mixing reaction tank. The bottom of the ammonia-mixing reaction tank is equipped with a discharge valve 89, and the discharge valve 89 is connected with a pump feed valve 90. The other end of the pump 91 is respectively equipped with a pump discharge valve 92, and a rotary discharge valve 93. The outlet of the pump discharge valve 92 is connected to the ammonia aspirator 99 through an inlet vane return valve 94 and is connected to the vane filter 96 through the vane filter feed valve 95. The vane filter is equipped with an overflow valve 98 and a discharge valve 97, and the discharge valve 97 is connected with the clear liquid reflux tank valve 87. Similarly, there are some necessary valves and connecting components for the manufacturing equipment, which are common technical means in the art and will not be described herein.

The ammonia-mixing desalination system can remove salt and other impurities in the mother liquor, and the operation process is simple. First, open the front control valve 85 of the safety valve, open the emptying valve 88, open the feed valve 83 to add the mother liquor to the ammonia-mixing reaction tank 82, and close the feed valve 83 after finishing feeding. Next, open the discharge valve 89 at the bottom of the tank, pump feed valve 90, inlet vane return valve 94, start pump 91, open pump discharge valve 92, stabilize and then open ammonia entering valve 84, and close the emptying valve 88, absorb ammonia to reach the content of 15% (mass to volume ratio, 15 g/100 ml) or more, then stop absorption, and the ammonia inlet valve 75 is closed; the vane filter overflow valve 98, the supernatant reflux tank valve 87, and the vane filter feed valve 95 are open. After the filter 96 is full, the vane filter discharge valve 97 is opened and the vane filter overflow valve 98 is closed at the same time such that the filtrate (last mother liquor) is returned to the ammonia-mixing reaction tank. During the cycle, samples are taken to observe the state of the material in the ammonia-mixing reaction tank 82 until the filtrate is clear. After the filtrate is clear, the transit and discharge valve 93 can be opened to transfer the treated last mother liquor to the aminolysis reaction step.

It should be noted that the said embodiments are only used to illustrate the technical solutions of this invention, and there is no limitation thereto; although this invention has been described in detail with reference to the foregoing embodiments, the ordinary technicians in this field should understand: the technical solutions described in the foregoing embodiments could be modified, or the reaction conditions could be replaced, or some of the technical features could be replaced by equivalents; and the modifications or substitutions shall not deviate from the technical solutions, spirit and scope of the embodiments of this invention.

While various embodiments of the present disclosure have been described in detail above, it will be understood that the components, features and configurations, as well as the methods of manufacturing the devices and methods described herein are not limited to the specific embodiments described herein.

What is claimed is:

1. A method for recovering and treating the last mother liquor of taurine in an ethylene oxide taurine production process, comprising the steps of:
    (a) adding alkali firstly and then acid to the last mother liquor of taurine to form a salt in the last mother liquor of taurine by the reaction of the alkali and acid, wherein the alkali is one or more of sodium hydroxide, potassium hydroxide, lithium hydroxide, sodium carbonate, potassium carbonate and lithium carbonate, and the acid is sulfuric acid, hydrochloric acid, or an organic acid;
    (b) concentrating and crystallizing the salt-containing last mother liquor of taurine obtained in step (a);
    (c) filtering the crystallized salt-containing last mother liquor of taurine obtained in step (b) to obtain a clear last mother liquor of taurine, wherein the generated salt reduces filtration resistance.

2. The method according to claim 1, wherein the salt in step (a) is formed by the addition of alkali followed by acid and the reaction temperature range of step (a) is from 50° C.-95° C., and the pH value of the last mother liquor after acid addition is between 7.0-10.5.

3. The method according to claim 2, wherein the amount of alkali added in step (a) is 5%-50% by volume of the volume of the last mother liquor of taurine.

4. The method according to claim 3, wherein the acid is sulfuric acid, and the alkali and sulfuric acid added in step (a) form sodium taurate and sodium sulfate in the last mother liquor.

5. The method according to claim 4, wherein 30%-60% water is condensed and evaporated in step (b), and the concentration is increased about 1.4-2.5 times, followed by cooling crystallization after the crystal solution is obtained.

6. The method according to claim 1, further comprising the steps of
    decolorizing the last mother liquor by adding activated carbon to the last mother liquor after the filtering of step (c), wherein the decolorization is under cooling conditions,
    lowering the PH to 9.0 to 10.5 by adding alkali, and
    filtering the last mother liquor.

7. The method according to claim 6, wherein the cooling conditions refers to the temperature during decolorization being lower than the temperature of the previous step, and the temperature of the last mother liquor is controlled to be 15-25° C.

8. The method according to claim 7, further comprising the steps of:
    subjecting the decolorized and filtered last mother liquor to ammonia-mixing treatment by adding ammonia thereto,
    separating the mother liquid from impurities by solid-liquid separation, and
    returning the mother liquid to an aminolysis step of the ethylene oxide taurine production process.

9. The method according to claim 8, wherein, during the ammonia-mixing treatment step, liquid ammonia or ammonia gas is added to the last mother liquor and the mass-to-volume ratio of ammonia is 15 g/100 ml or more.

10. An ethylene oxide process for producing taurine, comprising the steps of:
    (a) reacting ethylene oxide with sodium hydrogen sulfite solution to generate sodium isethionate;
    (b) subjecting the sodium isethionate generated in step (a) and the mother liquor removed of impurity and recovered in step (f) to an aminolysis reaction to generate a sodium taurate solution;
    (c) concentrating the sodium taurate solution of step (b) by evaporation;
    (d) generating crude taurine and a mother liquor by
        (i) acidifying the concentrated sodium taurate solution of step (c) using an acidic cation exchange resin to obtain a taurine solution, followed by concentration and crystallization of the taurine solution and thereafter separating the crude taurine from the mother liquor; or
        (ii) adding sulfuric acid to the concentrated sodium taurate solution of step (c) to obtain a taurine crystallization liquid, followed by cooling and crystallization of the taurine crystallization liquid and thereafter separating the crude taurine from the mother liquor;
    (e) concentrating and crystallizing the mother liquor from step (d) at least once, with taurine separated and extracted from the mother liquor after each crystallizing step, thereby generating the last mother liquor of taurine; and
    (f) performing the method of claim 1 to recover and treat the last mother liquor of taurine from step (e), and recycling the recovered and treated last mother liquor of taurine to step (b).

11. The method of claim 10, wherein step (e) is performed at least twice.

12. A production system for fully recovering taurine mother liquor and for treating the last mother liquor of taurine in an ethylene oxide process taurine production process, wherein the filtration resistance of the last mother liquor is reduced by a pretreatment system, wherein the pretreatment system includes a reaction device and/or a concentration device, a temperature reduction crystallization device, and a first filtration device that are sequentially connected;

and further wherein a discharge port of the pretreatment system is connected to an activated carbon decolorization and removing impurity device, wherein the activated carbon decolorization and removing impurity device comprises a decolorization tank and a second filter device, and further wherein the decolorization tank is provided with a feed port for adding activated carbon and alkali and a cooling mechanism for lowering the temperature inside the decolorization tank.

13. The production system according to claim 12, wherein a discharge port of the activated carbon decolorization and removing impurity device is connected to an ammonia-mixing desalination device, and the ammonia-mixing device includes an ammonia-mixing reaction tank and a closed filtration device provided with a circulation passage for returning filtrate to the ammonia-mixing reaction tank.

14. A method for recovering and treating the last mother liquor of taurine in an ethylene oxide taurine production process, comprising the steps of:
(a) directly adding salt formed by the reaction of alkali with acid to the last mother liquor of taurine, wherein the alkali is one or more of sodium hydroxide, potassium hydroxide, lithium hydroxide, sodium carbonate, potassium carbonate and lithium carbonate, and the acid is sulfuric acid, hydrochloric acid, or an organic acid;
(b) concentrating and crystallizing the salt-containing last mother liquor of taurine obtained in step (a);
(c) filtering the crystallized salt-containing last mother liquor of taurine obtained in step (b) to obtain a clear last mother liquor of taurine, wherein the added $Na_2SO_4$ reduces filtration resistance.

15. The method according to claim 14, wherein in step (a) 530 mol—5300 mol of $Na_2SO_4$ is added per 1 $m^3$ of the last mother liquor of taurine.

16. The method according to claim 14 further comprising the steps of:
decolorizing the last mother liquor by adding activated carbon to the last mother liquor after the filtering of step (c), wherein the decolorization is under cooling conditions,
lowering the PH to 9.0 to 10.5 by adding alkali, and filtering the last mother liquor.

17. The method according to claim 16, wherein the cooling conditions refers to the temperature during decolorization being lower than the temperature of the previous step, and the temperature of the last mother liquor is controlled to be 15-25° C.

18. The method according to claim 17, further comprising the steps of:
subjecting the decolorized and filtered last mother liquor to ammonia-mixing treatment by adding ammonia thereto,
separating the mother liquid from impurities by solid-liquid separation, and
returning the mother liquid to an aminolysis step of the ethylene oxide taurine production process.

19. The method according to claim 18, wherein, during the ammonia-mixing treatment step, liquid ammonia or ammonia gas is added to the last mother liquor and the mass-to-volume ratio of ammonia is 15 g/100 ml or more.

20. An ethylene oxide process for producing taurine, comprising the steps of:
(a) reacting ethylene oxide with sodium hydrogen sulfite solution to generate sodium isethionate;
(b) subjecting the sodium isethionate generated in step (a) and the mother liquor removed of impurity and recovered in step (f) to an aminolysis reaction to generate a sodium taurate solution;
(c) concentrating the sodium taurate solution of step (b) by evaporation;
(d) generating crude taurine and a mother liquor by
(i) acidifying the concentrated sodium taurate solution of step (c) using an acidic cation exchange resin to obtain a taurine solution, followed by concentration and crystallization of the taurine solution and thereafter separating the crude taurine from the mother liquor; or
(ii) adding sulfuric acid to the concentrated sodium taurate solution of step (c) to obtain a taurine crystallization liquid, followed by cooling and crystallization of the taurine crystallization liquid and thereafter separating the crude taurine from the mother liquor;
(e) concentrating and crystallizing the mother liquor from step (d) at least once, with taurine separated and extracted from the mother liquor after each crystallizing step, thereby generating the last mother liquor of taurine; and
(f) performing the method of claim 14 to recover and treat the last mother liquor of taurine from step (e), and recycling the recovered and treated last mother liquor of taurine to step (b).

* * * * *